United States Patent [19]

Zerbes et al.

[11] Patent Number: 4,886,892

[45] Date of Patent: Dec. 12, 1989

[54] PROCESS FOR THE PREPARATION OF OXIRANES

[75] Inventors: Rudolf Zerbes, Wuppertal, Fed. Rep. of Germany; Siegfried W. Linke, Seould, Rep. of Korea; Karl H. Mohrmann, Wuppertal, Fed. Rep. of Germany

[73] Assignee: Bayer Aktiengesellschaft, Leverkusen, Fed. Rep. of Germany

[21] Appl. No.: 7,078

[22] Filed: Jan. 27, 1987

Related U.S. Application Data

[60] Continuation of Ser. No. 760,025, Jul. 29, 1985, abandoned, which is a division of Ser. No. 603,478, Apr. 24, 1984, abandoned.

[30] Foreign Application Priority Data

Apr. 29, 1983 [DE] Fed. Rep. of Germany ....... 3315619

[51] Int. Cl.$^4$ ............................................. C07D 301/02
[52] U.S. Cl. ................................................. 549/519
[58] Field of Search ........................................ 549/519

[56] References Cited

U.S. PATENT DOCUMENTS 4,162,258 7/1979 Higo et al. ..................... 549/332
4,230,719 10/1980 Kodama et al. ................... 549/79

FOREIGN PATENT DOCUMENTS 40345 11/1981 European Pat. Off. .

OTHER PUBLICATIONS

C. Starks, Chemtech, (Feb. 1980), pp. 110–117.
V Franzen et al., Berichte, vol 96, (1963), pp. 1881–1890.
E. J. Corey et al., Jour. Am. Chem. Soc., vol. 87(6) (1965), pp. 1353–1364.
E. J. Corey et al., Jour. Am. Chem. Soc., vol. 84(19) (1962), pp. 3782–3783.
M. J. Bogdanowicz et al., Tetrahedron Letters, No. 10(1972), pp. 887–890.
Trost et al., Jour. Am. Chem. Soc., vol. 95(16) (1973), pp. 5311–5321.
T. Kutsuma et al., Heterocycles, vol. 8 (1977), pp. 397–401.
E. Borredon et al., Tetrahedron Letters, vol. 23(50) (1982), pp. 5283–5286.
C. Chambers et al., Modern Inorganic Chemistry, publ. by Butterworth & Co. Ltd. (1975), p. 130.
T. Kutsuma et al., Heterocycles, vol. 8 (1977) pp. 397–401.

*Primary Examiner*—Glennon H. Hollrah
*Attorney, Agent, or Firm*—Sprung, Horn, Kramer & Woods

[57] ABSTRACT

A process for the preparation of oxiranes is disclosed in which a ketone of the formula

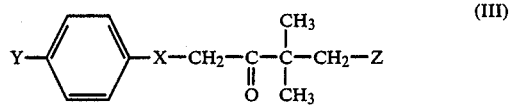

(III)

wherein Y represents chlorine or phenyl, X represents oxygen or $CH_2$ and Z represents hydrogen or halogen is reacted with trimethylsulphonium methyl sulphate formed by treating dimethyl sulphide with dimethyl sulphate. The process is carried out in the presence of potassium hydroxide or sodium hydroxide powder in an inert organic diluent at 0° to 60° C. The products are useful as intermediates for the formation of plant growth regulants and fungicides.

5 Claims, No Drawings

PROCESS FOR THE PREPARATION OF OXIRANES

This is a continuation of application Ser. No. 760,025 filed 7/29/85, which is a divisional of Ser. No. 603,478 filed 4/24/84, both now abandoned.

The present inventon relates to a new process for the preparation of known oxiranes which can be used as intermediates for the synthesis of compounds having plant-growth regulating and fungicidal activity.

It has already been disclosed that oxiranes can be prepared by reacting dimethyl sulphide and dimethyl sulphate and then reacting the trimethylsulphonium methyl sulphate, which is formed thereby as an intermediate, with carbonyl compounds in the presence of an inert organic solvent and in the presence of a strong base, such as butyl-lithium, sodium hydride, sodium amide, potassium tert.-butylate, sodium methylate or sodium ethylate (compare J. Amer. Chem. Soc. 87, 1353–1364 (1965) and Ber. 96, 1881 (1963)). Thus, for example, 2-(4-chlorophenoxymethyl)-2-tert.-butyloxirane can be prepared by reacting trimethylsulphonium methyl sulphate, prepared from dimethyl sulphide and dimethyl sulphate, in situ with 1-(4-chlorophenoxy)-3,3-dimethyl-2-butanone in acetonitrile in the presence of sodium methylate (compare EP-OS (European Published Specification) No. 40,345). The yields in this process are good. However, it is a disadvantage that all the bases used need to be specially prepared and are difficult to manipulate since they are sensitive to moisture and some of them are flammable.

It has also been disclosed that oxiranes are obtained when dimethyl sulphide is treated with dimethyl sulphate, and the trimethylsulphonium methyl sulphate thereby produced is reacted with carbonyl compounds in the presence of concentrated aqueous sodium hydroxide solution and an organic solvent which is poorly miscible with water and in the presence of a phase-transfer catalyst (compare Angew. Chem. 85, 867–868 (1973) and J. Org. Chem. 34, 2133 (1969)). However, hitherto only aldehydes have been converted into oxiranes using this process. In addition, the presence of a phase-transfer catalyst is always necessary in the system which consists of two liquid phases.

It has now been found that the known oxiranes of the formula

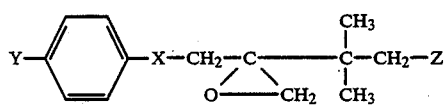
(I)

in which
Y represents chlorine or phenyl,
X represents oxygen or $CH_2$ and
Z represents hydrogen or halogen, are obtained when dimethyl sulphide is treated with dimethyl sulphate in the presence of an inert organic diluent, and trimethylsulphonium methyl sulphate, which is thereby produced, of the formula $$(CH_3)_3S^{\oplus} \quad CH_3SO_4^{\ominus} \quad \text{(II)}$$

is reacted, without previous isolation, with a ketone of the formula

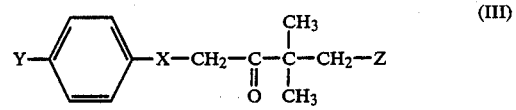
(III)

in which
X, Y and Z have the meanings indicated above, in the presence of potassium hydroxide or sodium hydroxide powder and in the presence of an inert organic diluent, at temperatures between 0° C. and 60° C.

It must be denoted extremely surprising that oxiranes of the formula (I) can be prepared by the process according to the invention in higher yields than by the processes hitherto known. Moreover, on the basis of the known state of the art, it had to be assumed that the presence of a phase-transfer catalyst would be necessary for this type of reaction of ketones which, of course, are generally less reactive than the corresponding aldehydes. However, this is not necessary, in contrast to expectation. The reaction takes place without problems even in the absence of a catalyst, although it is taking place in a system comprising a solid and a liquid phase. It is also surprising that the reaction according to the invention can be carried out without difficulty using sodium hydroxide or potassium hydroxide while the same reaction provides unsatisfactory results when powdered lithium hydroxide is used as the base.

The process according to the invention is distinguished by a number of advantages. Thus, the bases which can be used are also available on an industrial scale, are straightforward to manipulate and are not flammable. Furthermore, the oxiranes of the formula (I) are accessible in very high yields by this means.

The oxiranes which can be prepared according to the invention are defined by the formula (I). In this formula, X represents oxygen or the $CH_2$ group. Y represents chlorine orphenyl and Z preferably represents hydrogen, fluorine or chlorine.

When 1-(4-chlorophenoxy)-3,3-dimethyl-2-butanone is used as the starting material and potassium hydroxide powder is used as the base in the process according to the invention, then the course of the reaction can be illustrated by the diagram below:

(a)

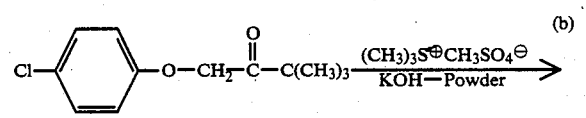
(b)

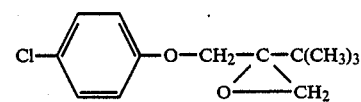

The ketones necessary as starting materials in the process according to the invention are defined by the formula (III). In this formula, Y represents chlorine or phenyl. X represents oxygen or the $CH_2$ group and Z preferably represents hydrogen, fluorine or chlorine.

The ketones of the formula (III) are known (compare German Patent Specification No. 2,201,063, DE-OS (German Published Specification) No. 2,705,678 and DE-OS (German Published Specification) No. 2,737,489).

The trimethylsulphonium methyl sulphate of the formula (II) which is also necessary as a starting material in the process according to the invention is likewise known (compare Heterocycles 8, 397 (1977)). It is employed in the above reaction in the freshly prepared state by producing it in situ by reaction of dimethyl sulphide with dimethyl sulphate.

The bases used in the process according to the invention are powdered potassium hydroxide or powdered sodium hydroxide.

All inert organic solvents can be used as the diluent for the process according to the invention, both for the preparation of the trimethylsulphonium methyl sulphate and for the subsequent reaction of the material with a ketone of the formula (III). Suitable and preferable are nitriles, such as acetonitrile, as well as polar solvents, such as dimethyl sulphoxide, also aliphatic or aromatic hydrocarbons, such as hexane, benzene, toluene or xylene, and finally alcohols, such as tert.-butanol and isopropanol and furthermore N-methylpyrrolidone.

On carrying out the process according to the invention, the reaction temperatures can be varied within a certain range. In general, both for the preparation of the trimethylsulphonium methyl sulphates and for its subsequent reaction with a ketone of the formula (III), temperatures between 0° C. and 60° C., preferably between 10° C. and 40° C., are used.

The process according to the invention is generally carried out under normal pressure. However, it is also possible to carry it out under elevated or reduced pressure.

On carrying out the process according to the invention, the amounts of the components in the reaction are generally selected such that 1.0 to 2.0 mole, preferably 1.0 to 1.5 mole, of dimethyl sulphate, 1.0 to 2.2 mole, preferably 1.0 to 1.6 mole, of dimethyl sulphide and 1.0 to 4.0 mole, preferably 1.5 to 2.0 mole, of potassium hydroxide or sodium hydroxide are employed for 1 mole of ketone of the formula (III).

The specific procedure for the process according to the invention is such that dimethyl sulphide and dimethyl sulphate are mixed in a solvent, then a solution of a ketone of the formula (III) in an organic solvent is added to this solution, and the particular required amount of base is subsequently added. Working up is carried out by customary methods. In general, the procedure is such that first the solvent is removed in vacuo, then oxidising agents, such as an aqueous hydrogen peroxide solution, dilute aqueous sodium hypochlorite or potassium hypochlorite solution, or together with a mixture of water and an organic solvent which is poorly miscible with water, are added to the residue remaining, and the organic phase is separated off, washed and evaporated after previous drying if necessary. The product resulting thereby can be distilled under reduced pressure for further purification.

The oxiranes of the formula (I) which can be prepared by the process according to the invention are valuable starting materials for the synthesis of 1-hydroxyethylazole derivatives which have outstanding plant-growth regulating and fungicidal properties (compare EP-OS (European Published Specification) No. 40,345).

Thus, for example, 2-(4-chlorophenoxymethyl)-3,3-dimethyl-1-(1,2,4-triazol-1-yl)-2-butanol of the formula

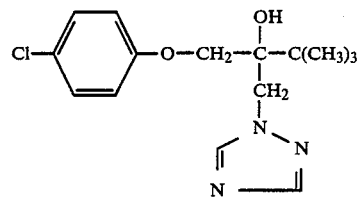

can be prepared by reacting 2-(4-chlorophenoxymethyl)-2-tert.-butyloxirane with 1,2,4-triazole in the presence of potassium hydroxide. This synthesis can be illustrated by the formulae below:

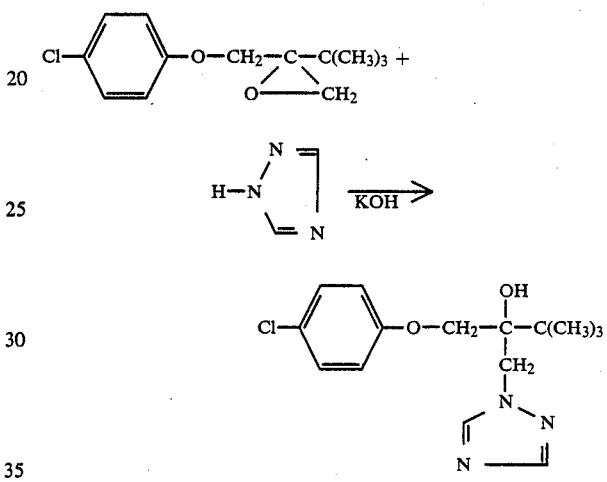

The process according to the invention is illustrated by the examples which follow.

Example.1

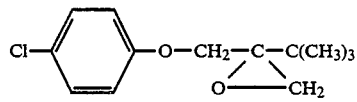

27 ml (0.375 mole) of dimethyl sulphide and 30 ml (0.317 mole) of dimethyl sulphate were added to 400 ml of acetonitrile at room temperature. This mixture was allowed to stand at room temperature for 12 hours for the formation of the trimethylsulphonium methyl sulphate and then a solution of 57 g (0.25 mole) of 1-(4-chlorophenoxy)-3,3-dimethyl-2-butanone in 100 ml of toluene was added dropwise with stirring. Then, with external cooling with ice-water and with stirring, 25.8 g (0.46 mole) of ground potassium hydroxide were added in portions. The mixture was stirred for a further 12 hours at room temperature and 400 ml of solvent were distilled out. The remaining mixture was cooled, 300 ml of a dilute aqueous solution of sodium hypochlorite were added and the mixture was stirred for 5 minutes. The organic phase was separated, washed twice with 100 ml of water each time and then evaporated under reduced pressure. A residue of 61.4 g remained, which, according to the gas chromatogram, consisted of 93.6% of 2-(4-chlorophenoxymethyl)-2-tert.-butyloxirane. A yield of 95.6% of theory was calculated from this.

Example 2

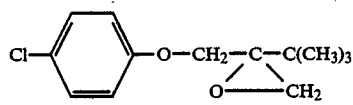

The procedure described in Example 1 was repeated, but 18.4 g (0.46 mole) of ground sodium hydroxide were now employed in place of potassium hydroxide. After working up, 57.8 g of a residue which, according to the gas chromatogram, consisted of 90.9% of 2-(4-chlorophenoxymethyl)-2-tert.-butyloxirane were obtained. A yield of 87.4% of theory was calculated from this.

Comparison example

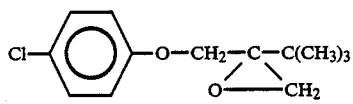

A solution of 162 ml (2.2 moles) of dimethyl sulphide in 400 ml of absolute acetonitrile was added to a solution of 189 ml (2.0 moles) of dimethyl sulphate in 1200 ml of absolute acetonitrile at room temperature. The reaction mixture was stirred overnight at room temperature. Then 118.8 g (2.2 moles) of sodium methylate were added. The mixture was stirred for 30 minutes and then a solution of 272 g (1.2 mole) of 1-(4-chlorophenoxy)-3,3-dimethyl-2-butanone in 600 ml of absolute acetonitrile was added dropwise within 30 minutes. The reaction mixture was then allowed to stand overnight. It was then evaporated, and the residue was partitioned between water and ethyl acetate, the organic phase was separated off, washed twice with water and once with saturated sodium chloride solution, dried over sodium sulphate, evaporated and the residue was distilled in vacuo.

242.4 g (84% of theory) of 2-(4-chlorophenoxymethyl)-2-tert.-butyloxirane of boiling point 115°-22° C./0.003 mm Hg column, of melting point 50°-52° C. were obtained. Example for the use of an oxirane which can be prepared according to the invention for the synthesis of a 1-hydroxyethylazole derivative having plant-growth regulating and fungicidal activity

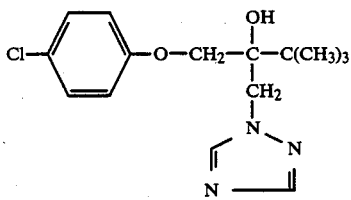

A mixture of 30 g of 2-(4-chlorophenoxymethyl)-2-tert.-butyloxirane, 9.8 g of 1,2,4-triazole and 1.2 g of solid potassium hydroxide in 70 ml of toluene and 7.5 ml of dimethyl sulphoxide was heated under reflux for 6 hours. After cooling to room temperature, 2 g of silica gel were added to the reaction mixture and it was then filtered. 75 ml of semi-concentrated hydrochloric acid were added to the filtrate, and the crystals which separated out thereby were filtered off with suction. Then 80 ml of water and aqueous sodium hydroxide solution were added to the crystalline solid so that the pH of the mixture was 13. It was stirred a further 2 hours at room temperature, then filtered off with suction and washed with water to neutrality. In this manner, 20 g (52% of theory) of 2-(4-chlorophenoxymethyl)-3,3-dimethyl-1-(1,2,4-triazol-1-yl)-2-butanol of melting point 84°-87° C. were obtained.

What is claimed is:

1. A process for the preparation of an oxirane of the formula

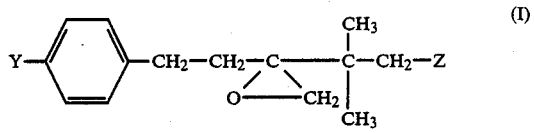

in which
Y represents chlorine and
Z represents hydrogen, consisting of contacting 1.0 to 1.6 moles of dimethyl sulphide with 1.0 to 1.5 moles of dimethyl sulphate in the presence of acetonitrile or toluene and contacting the resultant trimethylsulphonium methyl sulphate of the formula

with a ketone of the formula

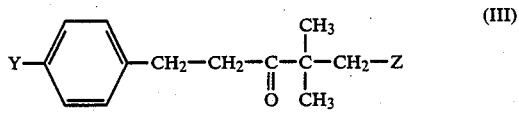

in which
Y and Z have the meanings indicated above, in the presence of 1.5 to 2.0 moles of potassium hydroxide or sodium hydroxide powder per mole of said ketone and in the presence of acetonitrile or toluene at a temperature between 10° C. and 40° C.

2. A process according to claim 1 wherein the process is carried out without isolating said trimethylsulphonium methyl sulphate.

3. A process according to claim 1, wherein said process is carried out under normal pressure.

4. A process according to claim 1, wherein said process is carried out under elevated pressure.

5. A process according to claim 1, wherein said process is carried out under reduced pressure.

* * * * *

UNITED STATES PATENT AND TRADEMARK OFFICE
CERTIFICATE OF CORRECTION

PATENT NO. : 4,886,892

DATED : December 12, 1989

INVENTOR(S) : Zerbes et al.

It is certified that error appears in the above-identified patent and that said Letters Patent is hereby corrected as shown below:

Title Page  [75] Inventors: After 3rd inventor delete " Wuppertal, Fed. Rep. of Germany " and insert -- Wolf Reiser, both of Wuppertal, Fed. Rep. of Germany --

Signed and Sealed this

Eighth Day of October, 1991

*Attest:*

HARRY F. MANBECK, JR.

*Attesting Officer*  *Commissioner of Patents and Trademarks*